United States Patent [19]

Beye et al.

[11] Patent Number: 5,723,647

[45] Date of Patent: Mar. 3, 1998

[54] N-(4-BROMO-2-FLUOROBENZYL) CARBAMATES AND A PROCESS FOR THEIR PREPARATION

[75] Inventors: Norbert Beye, Kelkheim; Karl-Ernst Mack, Wiesbaden, both of Germany

[73] Assignee: Hoechst Aktiengesellschaft, Germany

[21] Appl. No.: 717,013

[22] Filed: Sep. 20, 1996

[30] Foreign Application Priority Data

Sep. 21, 1995 [DE] Germany .................. 195 35 083.9

[51] Int. Cl.[6] .................................... C07C 271/10
[52] U.S. Cl. .................................. 560/30; 560/31
[58] Field of Search ........................ 560/30, 31

[56] References Cited

FOREIGN PATENT DOCUMENTS 70 03 770  1/1995  Japan .
WO 94/10132  5/1994  WIPO .

OTHER PUBLICATIONS

Chemical Abstracts, vol. 72, 132344m, p. 327.
Ogawva, K., et al, *Eur. J. Med. Chem.* 28:769–781 (1993).

*Primary Examiner*—Joseph Conrad
*Attorney, Agent, or Firm*—Connolly and Hutz

[57] ABSTRACT

N-(4-Bromo-2-fluorobenzyl)carbamates and a process for their preparation

The invention relates to N-(4-bromo-2-fluorobenzyl)carbamates of the formula (I),

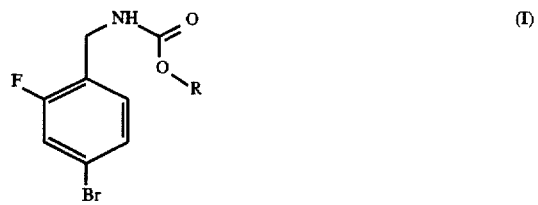

where R is $(C_1-C_{12})$alkyl, benzyl or phenyl, where the benzyl and phenyl radicals can also be substituted by $(C_1-C_3)$alkyl or $(C_1-C_3)$alkoxy, and to a process for preparing these compounds.

11 Claims, No Drawings

N-(4-BROMO-2-FLUOROBENZYL) CARBAMATES AND A PROCESS FOR THEIR PREPARATION

The invention relates to N-(4-bromo-2-fluorobenzyl) carbamates and a process for their preparation.

The novel N-(4-bromo-2-fluorobenzyl)carbamates are starting products for nitrogen-containing heterocycles, pharmaceutical intermediates and crop protection agents. Compounds of this type are of importance, in particular in the synthesis of novel aldose-reductase inhibitors. (K. Ogawva, I. Yamawaki, Y. I. Matsusita, N. Nomura, P. F. Kador, J. H. Kinoshita, Eur. J. Med. Chem. 28, 769, (1993)).

In the patent application WO 94 10 132 A1, substituted benzylcarbamates having herbicidal properties are described. The synthesis of N-benzylcarbamates is reported in JP 70 03 770 [C.A. 72: 132344m (1970)].

There was therefore a need to provide novel compounds of this substance class in order, on the one hand, to increase the range of synthetic methods of previously known products and, on the other hand, to make novel products accessible.

This object is achieved by N-(4-bromo-2-fluorobenzyl) carbamates of the formula I,

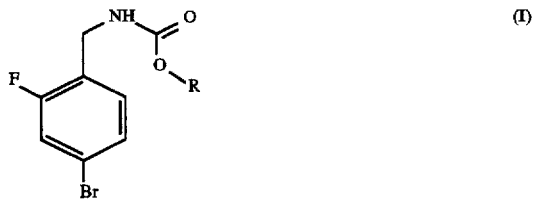

(I)

where R is $(C_1-C_{12})$alkyl, benzyl or phenyl, where the benzyl and phenyl radicals can also be substituted by $(C_1-C_3)$alkyl or $(C_1-C_3)$alkoxy.

Of particular interest are compounds of the formula (I), in which R is $(C_1-C_4)$alkyl, benzyl or methoxybenzyl.

Important compounds are O-benzyl N-(4-bromo-2-fluorobenzyl)carbamate, O-methyl N-(4-bromo-2-fluorobenzyl)carbamate, O-ethyl N-(4-bromo-2-fluorobenzyl)carbamate, O-p-methoxybenzyl N-(4-bromo-2-fluorobenzyl)carbamate, O-butyl N-(4-bromo-2-fluorobenzyl)carbamate.

The invention further relates to a process for preparing compounds of the formula (1), which comprises reacting a 4-bromo-2-fluorobenzyl halide with an alkali metal cyanate or ammonium cyanate in a dipolar aprotic solvent in the presence of the alcohol ROH.

It has proved to be useful in this case to use 4-bromo-2-fluorobenzyl bromide, potassium cyanate and, as solvent, DMF, and to employ a temperature of 30° to 150° C., in particular 80° to 140° C., preferably 100° to 120° C.

The reaction generally concludes within 1 to 3 h. It has proved to be expedient to use the cyanate and the alcohol in excess, in particular a usage rate of 1.1 to 3 mol of cyanate and 1.1 to 4 mol of alcohol per mole of benzyl halide has proved to be useful.

The following examples serve to illustrate the invention, without restricting it thereto.

EXAMPLE 1

Synthesis of O-benzyl N-(4-bromo-2-fluorobenzyl) carbamate

Anhydrous and amine-free DMF (180 ml) and benzyl alcohol (28 ml) and KOCN (0.247 mol, 20 g) are charged into a 500 ml 2-neck round bottom flask having a reflux condenser and drying tube. A solution of 4-bromo-2-fluorobenzyl bromide (0.075 mol, 20 g) in DMF (20 ml) is added rapidly (in the course of 1 min) at room temperature to the stirred reaction mixture by means of a dropping funnel. The resulting suspension is subsequently heated with stirring to approximately 110° C. and further stirred at this temperature for approximately 1.5 h. The mixture is then cooled to room temperature. The salt present in the reaction mixture is filtered off by suction via a frit. The solvent and excess benzyl alcohol are removed from the filtrate in vacuo. The light yellow oily residue is cooled with ice for crystallization. The bright crystalline mass produced is washed with water, filtered and dried. Yield: 23.2 g (:91.5% of theory) M.p.: 82°–84° C. GC/MS: $M^+$=337, IR in KBr [$cm^{-1}$]: 3342 (m) N—H, 1689 (s) C=O, 1535 (m) NH—C, 1276 (m) C—O—C

EXAMPLE 2

Synthesis of O-methyl N-(4-bromo-2-fluorobenzyl) carbamate

Anhydrous and amine-free DMF (500 ml) and methanol (50 ml) and KOCN (0.62 mol, 50 g) are charged into a 1000 ml 2-neck round bottom flask having a reflux condenser and drying tube. A solution of 4-bromo-2-fluorobenzyl bromide (0.186 mol, 50 g) in DMF (50 ml) is added rapidly at room temperature to the stirred reaction mixture by means of a dropping funnel. The resulting suspension is subsequently heated with stirring to approximately 100° C. and further stirred at this temperature for approximately 1.5 h. The mixture is then cooled to room temperature. The salt present in the reaction mixture is filtered off by suction via a frit. The solvent and excess methanol are removed from the filtrate in vacuo. The oily residue is cooled for crystallization. The bright crystalline mass produced is washed with water, filtered and dried. Yield: 44.3 g (91% of theory) M.p.: 66°–67.5° C. GC/MS: $M^+$=261, IR in KBr [$cm^{-1}$]: 3338 (m) N—H, 1694 (s) C=O, 1536 (m) NH—C, 1280 (m) C—O—C Further O-organyl N-(4-bromo-2-fluorobenzyl) carbamates were prepared in a similar manner to Example 1:

| Ex. No. | Formula (I) R | Alcohol | Yield [%] | M.p. [°C.] | MS | IR (KBr) [$cm^{-1}$] |
|---|---|---|---|---|---|---|
| 3 | ethyl | ethanol | 89 | 39–43 | 275 | 3317 (m) N-H, 1686 (s) C = O, 1534 (m) NH-C, 1280 (m) C-O-C |
| 4 | n-butyl | n-butanol | 85 | waxy | 303 | 3318 (m) N-H, 1695 (s) C = O, 1536 (m) NH-C, 1257 (m) C-O-C |
| 5 | p-methoxy-benzyl | p-anisyl alcohol | 89 | 88–90 | 367 | 3338 (m) N-H, 1686 (s) C = O, 1536 (m) NH-C, 1278 (m) C-O-C |

We claim:

1. An N-(4-bromo-2-fluorobenzyl)carbamate of the formula (I),

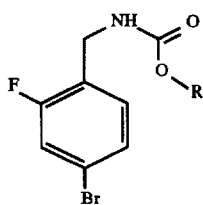

(I)

where R is $(C_1-C_{12})$alkyl, benzyl or phenyl, where the benzyl and phenyl radicals can also be substituted by $(C_1-C_3)$alkyl or $(C_1-C_3)$alkoxy.

2. A compound as claimed in claim 1, wherein in formula (I) R is $(C_1-C_4)$alkyl, benzyl or methoxybenzyl.

3. A compound as claimed in claim 1, wherein formula (I) is O-benzyl N-(4-bromo-2-fluorobenzyl)carbamate, O-methyl N-(4-bromo-2-fluorobenzyl)carbamate, O-ethyl N-(4-bromo-2-fluorobenzyl)carbamate, O-p-methoxybenzyl N-(4-bromo-2-fluorobenzyl)carbamate or O-butyl N-(4-bromo-2-fluorobenzyl)carbamate.

4. A process for preparing compounds of the formula (I), which comprises reacting a 4-bromo-2-fluorobenzyl halide with an alkali metal cyanate or ammonium cyanate in a dipolar aprotic solvent in the presence of the alcohol ROH.

5. The process as claimed in claim 4, wherein the 4-bromo-2-fluorobenzyl halide used is a bromide.

6. The process as claimed in claim 4, wherein the cyanate used is potassium cyanate.

7. The process as claimed in claim 4, wherein the solvent used is DMF.

8. The process as claimed in claim 4, wherein the reaction is carried out at a temperature of 30° to 150° C.

9. The process as claimed in claim 4, wherein 1.1 to 3 mol of cyanate and 1.1 to 4 mol of alcohol are used per mole of benzyl halide.

10. The process as claimed in claim 4, wherein the reaction is carried out at a temperature of 80° to 140° C.

11. The process as claimed in claim 4, wherein the reaction is carried out at a temperature of 100° to 120° C.

* * * * *